United States Patent [19]

Lau et al.

[11] Patent Number: 5,373,724
[45] Date of Patent: Dec. 20, 1994

[54] METHOD OF SENSING A GAS CONCENTRATION

[75] Inventors: James C. Lau; Charles C. Ruth, both of Torrance, Calif.

[73] Assignee: TRW Inc., Redondo Beach, Calif.

[21] Appl. No.: 155,403

[22] Filed: Nov. 19, 1993

Related U.S. Application Data

[62] Division of Ser. No. 894,684, Jun. 2, 1992, abandoned.
[51] Int. Cl.⁵ .................... G01N 11/04; G01N 1/22
[52] U.S. Cl. .................. 73/23.2; 73/864.63; 73/864.83
[58] Field of Search .............. 73/23.2, 864.51, 864.63, 73/864.83, 864.91, 864.52; 422/103, 104; 436/181

[56] References Cited

U.S. PATENT DOCUMENTS

| | | | |
|---|---|---|---|
| 3,290,119 | 12/1966 | Ohlgren et al. | 73/31.03 |
| 3,304,977 | 2/1967 | Hammons | 73/864.51 |
| 3,533,272 | 10/1970 | Dahms | 73/31.03 |
| 4,988,428 | 1/1991 | Iwakiri et al. | 204/153.14 |
| 4,994,117 | 2/1991 | Fehder | 436/133 |
| 5,007,988 | 4/1991 | Archer et al. | 204/153.18 |

*Primary Examiner*—Hezron E. Williams
*Assistant Examiner*—Michael J. Brock

[57] ABSTRACT

A resealable gas concentration sensor for determining the concentration of a particular gas within a gaseous environment. The sensor is constructed of a housing and a cap. The cap is adapted to be temporarily coupled with the housing while in the environment to define a sealed sample chamber, thereby capturing a sample of the environment. A venturi tube having a narrow passage is affixed to the housing which is adapted to allow fluid flow through venturi tube into test equipment for determining the concentration of the gas in the sample. The housing and cap may be repeatedly uncoupled and resealed to capture additional samples and measure other concentrations.

15 Claims, 3 Drawing Sheets

METHOD OF SENSING A GAS CONCENTRATION

This is a division of U.S. patent application Ser. No. 07/894,684, filed Jun. 2, 1992, abandoned.

BACKGROUND OF THE INVENTION

1. Technical Field

This invention relates generally to a gas concentration sensor, and more particularly to a resealable device for measuring the concentration of a gas in an environment.

2. Discussion

Various industrial operations must be conducted in a specific gaseous environment. For example, some United States military specifications require that products be sealed in an environment other than air, which includes an indicator gas, such as helium or argon. One purpose for this requirement is to facilitate testing to determine whether the products are sufficiently sealed to prevent entry or escape of a gas, or even moisture.

Apparatus for conducting these operations is shown in FIG. 1 and consists of a sealed environment chamber 10 containing a gaseous environment 12 and having a pair of operator's gloves 14, 16 for manipulating objects and tools inside environment 12 by an operator outside of chamber 10. Chamber 10 is coupled to an environment regulation system having an inlet tube 18 and an outlet tube 20 for regulating the composition of, particularly the concentration of a gas in, the gaseous environment 12. Gaseous environment 12 consists generally of inert gaseous components with one type of gas, such as helium, in a specific concentration. Chamber 10 is further provided with a lock chamber 22 containing a lock environment 23 and having an inner and outer door 24, 26 and being equipped with a lock regulation system having an inlet tube 28 and an outlet tube 30 for regulating the composition of the gaseous lock environment, including the lock concentration of a gas, contained within lock chamber 22.

Objects may be placed within environment 12 without substantially altering the composition of environment 12 by opening outer door 26, inserting the object within lock chamber 22, closing outer door 26, using lock regulation system to make lock environment 23 within lock chamber 22 substantially similar to environment 12 within environment chamber 10, opening inner door 24, and placing the object within environment 12. Environment 12 is thereby maintained having a substantially constant gaseous composition while the object is transferred to environment chamber 10. Objects may be removed from environment 12 by reversing the process.

Devices for measuring a gas concentration in an environment chamber generally involve capturing a sample of the environment within a sealed sample chamber. The sample chamber requires a seal which is capable of maintaining an ultra-high vacuum to accurately measure the gas concentration. As a result, prior sensing devices generally were permanently sealed, such as by pinching off a malleable access tube or by welding. These devices may be used only once and are capable of taking only one measurement.

It is therefore desirable to measure the concentration of a gas in an environment with a sensing device which is not permanently sealed and which can make repeated measurements, as well as measure concentrations in multiple environment chambers.

SUMMARY OF THE INVENTION

According to a preferred embodiment of the present invention, a resealable gas concentration sensor is disclosed having a housing and a cap adapted to be temporarily coupled together in a gaseous environment so that a sample of the environment is captured within a sample chamber defined by the temporarily sealed housing and cap. A tubular member having a narrow passage is coupled to the housing and allows the sample to flow from the sample chamber to test equipment for measuring the concentration of a gas in the sample.

The cap and housing may be repeatedly uncoupled and resealed in order to capture additional samples and make repeated measurements.

BRIEF DESCRIPTION OF THE DRAWINGS

The various advantages and features will become apparent from the following description and claims in conjunction with the accompanying drawings:

DETAILED DESCRIPTION OF THE PREFERRED EMBODIMENTS

The following description of the preferred embodiments is merely exemplary in nature and is in no way intended to limit the invention or its application or uses.

Figure 1:
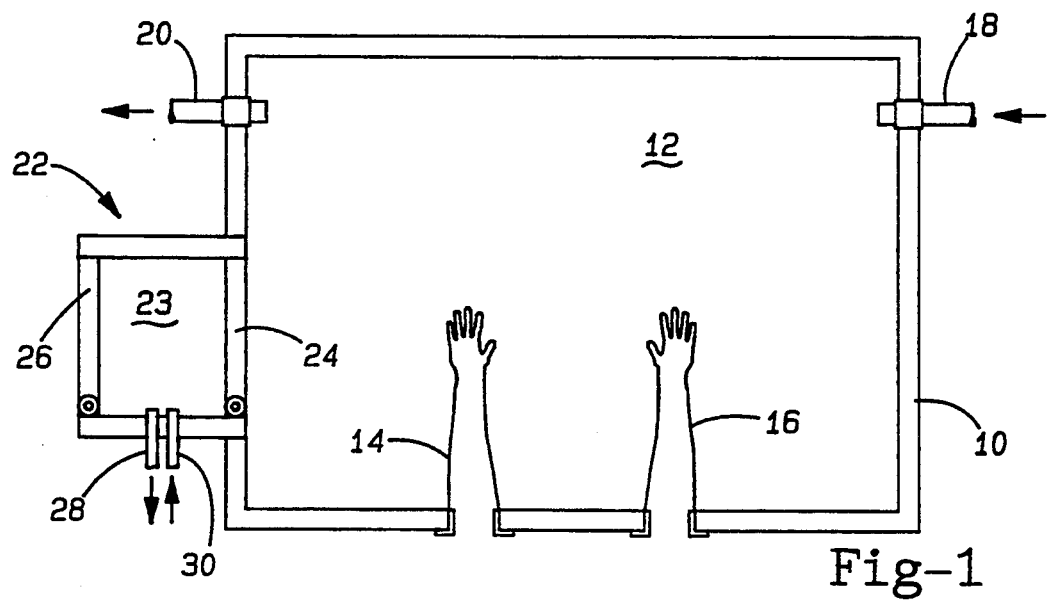
FIG. 1 is an environment chamber according to the prior art.
Figure 2:
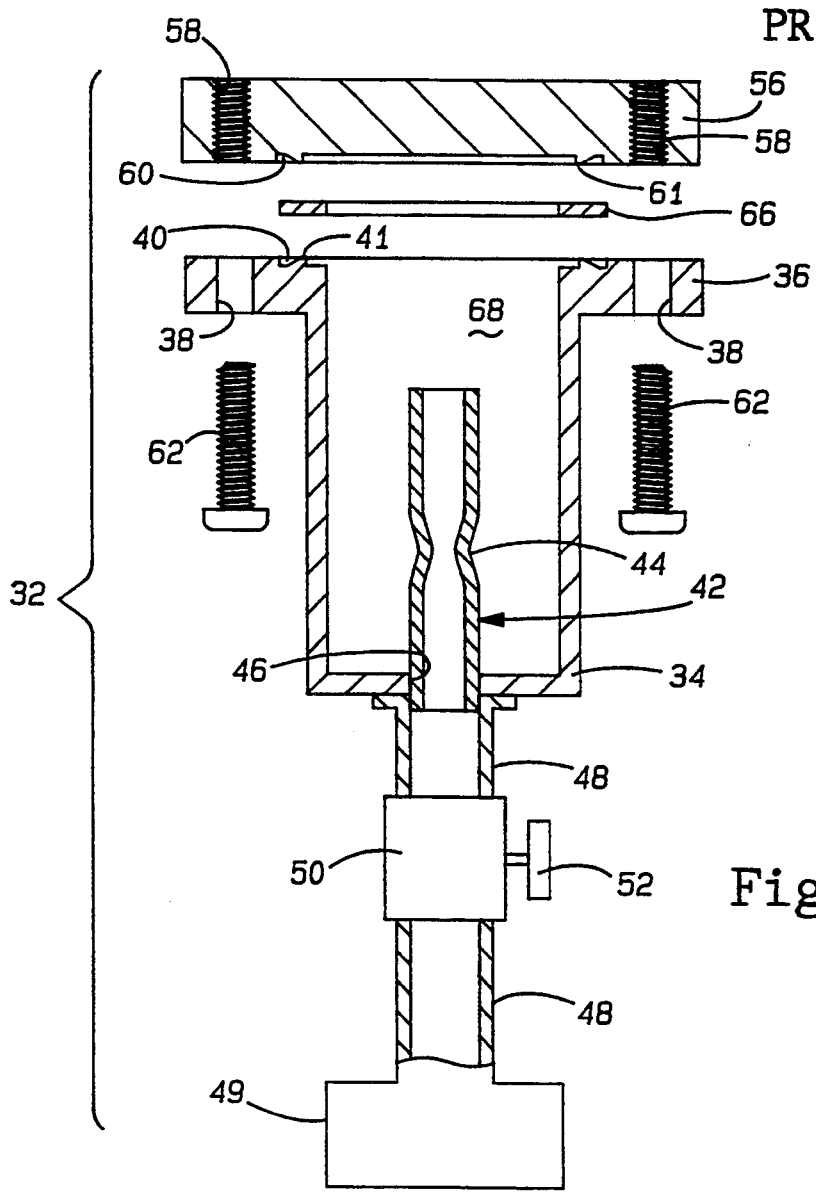
FIG. 2 is cut-away view of a gas concentration sensor according to a preferred embodiment of the present invention.
Figure 3:
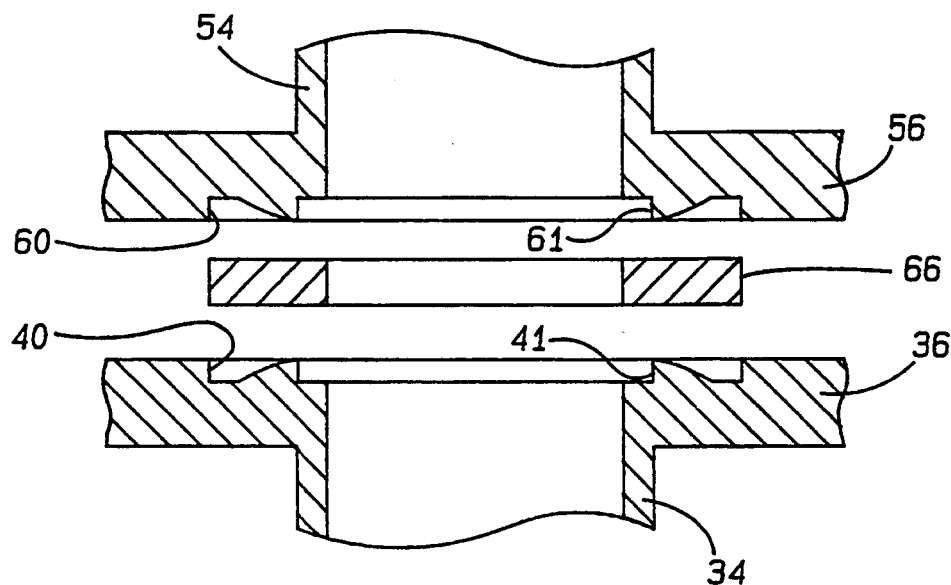
FIGS. 3 and 4 are partial cut-away views of a portion of a preferred embodiment of the present invention.

Referring to the drawings, a gas concentration sensor 32 is shown in FIG. 2 and is constructed of a housing 34 having a flange 36 formed with a plurality of bores 38 and a recess 40 formed in the top surface of flange 36. Recess 40 is formed with a wedge-shaped portion 41 having an edge and extending around the circumference of recess 40. A venturi tube 42 having a narrow passage 44 is inserted within an opening 46 formed at the lower end of housing 34 and is affixed therein. Narrow passage 44 restricts fluid flow through tube 42. The configuration of housing 34 surrounds and thereby prevents damage to the relatively delicate venturi tube 42. As a result, tube 42 is located in a position in which it is difficult to damage. Tube 42 is connected with an access tube 48 which is coupled to test equipment 49, such as a "leak detector", for measuring a flow rate of a gas through access tube 48 and thus through tube 42. A suitable "leak detector" is a mass spectrometer which is tuned to the specific mass to charge ratio of the gas which is to be measured, as is known in the art.

Venturi tube 42 may be constructed by any of several methods known in the prior art. One method is to soften a portion of a glass tube, for example by heating. Then opposing ends of the tube are drawn apart and twisted in opposite directions, reducing the softened portion to a very small diameter. Narrow passage 44 is preferably within the range of 1 to 10 microns.

Sensor 32 further consists of a cap or blank flange 56, the perimeter of which is similar to flange 36 formed on homing 34. A blank flange is defined as a plate-shaped member, as opposed to a container which defines an interior volume. Flange 56 is formed with a plurality of threaded bores 58 and a recess 60 in the lower surface of flange 56. Recess 60 is formed with a pointed, wedge-shaped portion 61 similar to wedge 41 in recess 40 on flange 36.

Housing 34 and flange 54 may be temporarily coupled together by inserting bolts 62 through bores 38 and then through threaded bores 58. Housing 34 and Flange 54 may thus be repeatedly coupled and uncoupled.

Figure 4:
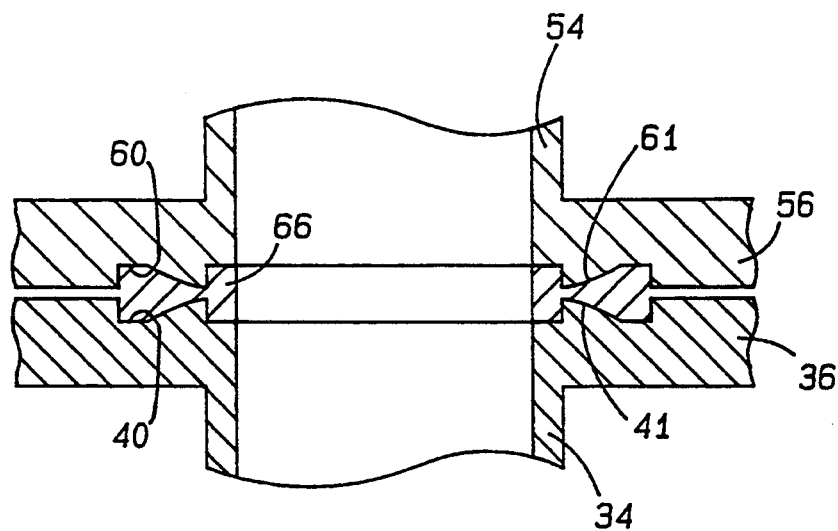

A seal gasket 66 is preferably inserted between housing 34 and flange 54 when they are coupled together. Gasket 66 is inserted into place in recesses 40, 60; and wedges 41, 61 partially crush opposing faces of gasket 66, as shown in FIG. 4. When housing 34 and flange 54 are coupled, a sealed sample chamber 68 is created. Flanges 41, 61 and partially crushed gasket 66 thus prevent gases contained within the temporarily sealed sample chamber 68 from leaking. Although housing 34 and flange 54 may be repeatedly sealed and resealed, gasket 66 may only be used once became it is permanently deformed and crushed during use. Gasket 66 is preferably manufactured of oxidation-free high conductivity copper. High purity aluminum is also acceptable.

Sensor 32 may also be equipped with a valve 50 operated by a valve handle 52 for selectively allowing or preventing fluid flow through access tube 48. Valve 50 enables sensor 32 to be removed from environment 12 before coupling sensor 32 to test equipment 49. Valve 50 further allows a sensor 32 containing a sample to be sealed for a period of time or transported to another location for calibration. As a result, valve 50 enables a sealed sensor 32 to be removed from environment chamber 10 and transported to a testing site for cross-calibration or equipment performance comparisons.

Housing 34, flange 54, access tube 48, and valve 50 are preferably constructed with low outgassing materials, such as stainless steel, which prevent escape of any gases contained within sample chamber 68 and prevent entry into sample chamber 68 by gases outside of sensor 32.

In operation of gas concentration sensor 32, the sample within sample chamber 68 consists of at least one inert gas, with one type of indicator gas being in a specific concentration. The sample flows through tube 42 into test equipment 49. Narrow passage 44 restricts this flow and allows the sample to flow through tube 42 from sample chamber at a rate in proportion to a concentration of a gas contained within sample chamber. In other words, the sealed sensor 32 is hermetic except for a "calibrated leak" which is allowed to flow through tube 42. The concentration of the gas in sample chamber 68 may consequently be calculated by measuring the flow rate through tube 42 and access tube 48.

Flow through tube 42 under steady flow conditions will be governed by the following equation:

$$R = fLC \qquad (1)$$

where R represents the measured flow rate through tube 42;

f equals a conversion factor defined as the square root of the quotient of the molecular weight of air divided by the molecular weight of the gas;

$$f = \sqrt{\frac{M_{air}}{M_{gas}}} \qquad (2)$$

L equals a structural coefficient which is dependent on the physical configuration of a particular sensor 32, which may be determined by using known values of C and f, measuring R, and solving equation (1) for L for a particular device; and C equals the concentration of the gas in the sample.

Where helium is selected, the gas to air conversion factor (f) is determined by solving equation (2) and equals approximately 2.68.

$$f = \sqrt{\frac{M_{air}}{M_{He}}} = \sqrt{\frac{28.8}{4.00}} = 2.68 \qquad (3)$$

The value of L for any particular sensor 32 with respect to helium may be determined by filling a sealed sample chamber 68 in sensor 32 with pure helium, in which case the helium concentration (C) would equal 1.0. As a result, after measuring the flow rate (R), L becomes the only remaining variable in equation (1), and L may be calculated.

After determining the value of L with respect to helium for a particular sensor 32, the concentration of helium in an environment 12 may be determined by capturing a sample of the gas in environment 12 within sample chamber 68. Tube 42 will allow the sample to escape into test equipment 49 at a particular flow rate R. Because the values of L and f would now be known in this example, and after measuring R under substantially steady flow conditions, the only remaining variable in equation (1) becomes the sample concentration of helium (C). The helium concentration in the gaseous sample contained within sample chamber 68 may thus be determined by solving equation (1) for helium concentration:

$$C = \frac{R}{fL} \qquad (4)$$

Figure 5:
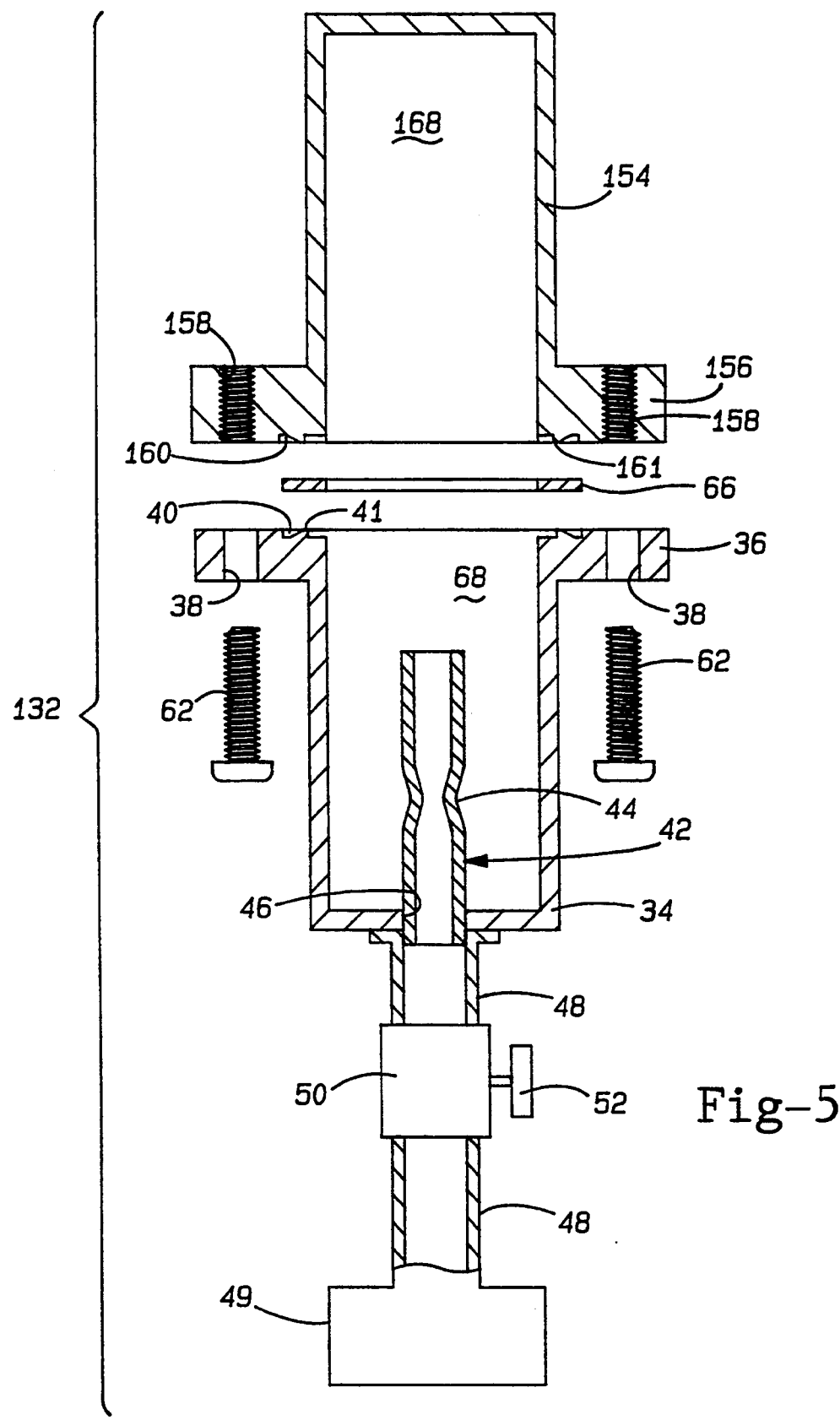
FIG. 5 is a cut-away view of an alternative embodiment of the present invention.

An alternative embodiment of sensor 32 is shown in FIG. 5, in which elements corresponding with those shown in FIG. 2 are referenced identically. Sensor 132 includes a container 154 having a flange 156 with a plurality of threaded bores 158 and a recess 160 having a pointed, wedge-shaped portion 161 in the lower surface of flange 156. Container 154 forms a larger chamber 168 than chamber 68. The size of chamber 68 may also be altered by changing the dimensions of housing 34.

It should be understood that an unlimited number of configurations of the sensor can be realized which satisfy the requirements described above. The foregoing discussion discloses and describes merely exemplary embodiments of the present invention. One skilled in the art will readily recognize from this discussion and from the accompanying drawings and claims, that various changes, modifications and variations can be made without departing from the spirit and scope of the invention, as defined in the following claims.

What is claimed is:

1. A method for determining a concentration of a gas in a gaseous environment, comprising the steps of:
    a) placing a sensing device into said environment, said sensing device being formed of a housing and a separate cap, a tubular member being affixed to said housing and having an inlet inside the housing and an outlet outside the housing, said tubular member defining a flow restricting passage which is more narrow than a remainder of said tubular member;

b) temporarily coupling said housing and cap together in said environment so as to define a temporarily sealed sample chamber, thereby capturing a sample of said environment having a sample concentration which is approximately equivalent to said concentration;

c) allowing said sample to flow through said flow restricting passage and to escape said sample chamber at a flow rate which is in proportion to said sample concentration, and simultaneously preventing said sample from escaping said sample chamber except through said flow restricting passage;

d) measuring said flow rate with testing equipment coupled to said tubular member;

e) calculating said sample concentration from said flow rate; and f) uncoupling said housing and cap so that said sensing device may be used to capture and measure additional samples.

2. The method of claim 1, further comprising the step following said step a) of placing a seal gasket between said housing and said cap.

3. The method of claim 2, wherein said step b) further comprises partially crushing said gasket around a perimeter thereof, to more effectively seal said sample chamber.

4. The method of claim 3, wherein said housing and cap each have mutually opposing surfaces, a wedge portion extending from said surfaces for performing said step of partially crushing said gasket.

5. The method of claim 2, wherein said seal gasket is formed of oxidation free high conductivity copper.

6. The method of claim 1, wherein said step b) is performed by fastening together a first and second flange formed respectively on said housing and cap with a plurality of fasteners for holding said flanges together.

7. The method of claim 1, wherein said flow restricting passage has a diameter substantially within the range of 1 to 10 microns.

8. The method of claim 1, further comprising the steps following said step b) of:

closing a valve coupled to said outlet of said tubular member, said valve operative to substantially prevent fluid flow through said tubular member;

removing said sensing device from said environment; and opening said valve.

9. The method of claim 1, wherein said step e) is accomplished by solving the following equation:

$$C = R/(fL)$$

where C equals said sample concentration;

R equals said flow rate;

f equals a conversion factor defined as a square root of a quotient of a molecular weight of air divided by a molecular weight of said gas; and L equals a structural coefficient which is dependent on a physical configuration of said device, determined by using known values of C and f, measuring R, and solving the above equation for a particular device.

10. The method of claim 1, wherein said cap is plate-shaped.

11. The method of claim 1, wherein said housing surrounds and protects said tubular member.

12. A method for determining a concentration of a gas in a gaseous environment, comprising the steps of:

a) placing a sensing device into said environment, said sensing device being formed of a housing and a separate cap, a tubular member being affixed to said housing and having an inlet inside the housing and an outlet outside the housing, said tubular member defining a flow restricting passage which is more narrow than a remainder of said tubular member;

b) placing a seal gasket between said housing and said cap;

c) temporarily coupling said housing and cap together in said environment so as to define a temporarily sealed sample chamber, thereby capturing a sample of said environment having a sample concentration which is approximately equivalent to said concentration, said temporarily sealed housing and container partially crushing said gasket around a perimeter thereof to more effectively seal said sample chamber;

d) closing a valve coupled to said outlet of said tubular member to substantially prevent fluid flow through said tubular member;

e) removing said sensing device from said environment;

f) opening said valve;

g) allowing said sample to flow through said flow restricting passage and to escape said sample chamber at a flow rate which is in proportion to said sample concentration, and simultaneously preventing said sample from escaping said sample chamber except through said flow restricting passage;

h) measuring said flow rate with testing equipment coupled to said tubular member;

i) calculating said sample concentration from said flow rate; and j) uncoupling said housing and cap so that said sensing device may be used to capture and measure additional samples.

13. The method of claim 12, wherein said housing and cap each have mutually opposing surfaces, a wedge portion extending from said surfaces for performing said step of partially crushing said gasket.

14. The method of claim 12, wherein said step c) is performed by fastening together a first and second flange formed respectively on said housing and cap with a plurality of fasteners for holding said flanges together.

15. The method of claim 12, wherein said step i) is accomplished by solving the following equation:

$$C = R/(fL)$$

where C equals said sample concentration;

R equals said flow rate;

f equals a conversion factor defined as a square root of a quotient of a molecular weight of air divided by a molecular weight of said gas; and L equals a structural coefficient which is dependent on a physical configuration of said device, determine by using known values of C and f, measuring R, and solving the above equation for a particular device.

* * * * *